US00PP26971P3

(12) United States Plant Patent
Wright et al.

(10) Patent No.: US PP26,971 P3
(45) Date of Patent: Jul. 26, 2016

(54) BLUEBERRY PLANT NAMED 'C04-014'

(50) Latin Name: ***Vaccinium corymbosum* hybrid**
Varietal Denomination: C04-014

(71) Applicants: CostaExchange Pty Ltd., Corindi (AU); Florida Foundation Seed Producers, Inc., Marianna, FL (US)

(72) Inventors: Gary Wright, Corindi Beach (AU); Paul Lyrene, Micanopy, FL (US)

(73) Assignees: COSTAEXCHANGE PTY LTD., Corindi (AU); FLORIDA FOUNDATION SEED PRODUCERS, INC., Marianna, FL (US)

( * ) Notice: Subject to any disclaimer, the term of this patent is extended or adjusted under 35 U.S.C. 154(b) by 0 days.

(21) Appl. No.: 13/999,604

(22) Filed: Mar. 12, 2014

(65) Prior Publication Data

US 2014/0283232 P1 Sep. 18, 2014

Related U.S. Application Data

(60) Provisional application No. 61/851,672, filed on Mar. 12, 2013.

(51) Int. Cl.
*A01H 5/08* (2006.01)

(52) U.S. Cl.
USPC ..... Plt./157
CPC ..... *A01H 5/08* (2013.01)

(58) Field of Classification Search
USPC ..... Plt./157
See application file for complete search history.

(56) References Cited

U.S. PATENT DOCUMENTS

PP10,675 P 11/1998 Lyrene

*Primary Examiner* — Annette Para
(74) *Attorney, Agent, or Firm* — Hahn Loeser & Parks, LLP

(57) ABSTRACT

A new and distinct cultivar of blueberry (*Vaccinium corymbosum* hybrid) plant named 'C04-014,' characterized by its semi-upright plant shape and strong plant growth vigor, late timing of fruiting, medium to large fruit size, firm fruit suited to handling, good fruit flavor. This combination results in higher quality fruit with a later availability than other varieties.

4 Drawing Sheets

Latin name of the family, genus, and species: Family—Ericaceae. Genus—*Vaccinium.* Species—*corymbosum* hybrid.

Variety denomination: The new blueberry plant claimed is of the variety denominated 'C04-014.'

BACKGROUND OF THE INVENTION

The present invention relates to a new and distinct perennial variety of *Vaccinium corymbosum* hybrid (blueberry), which has been given the variety denomination of 'C04-014.' The new variety 'C04-014' was selected from a population of seedlings derived from crossing the blueberry variety known as 'Star' (seed parent) (U.S. Plant Pat. No. 10,675) and the variety known as 'C96-97' (pollen parent) (not patented). The cross was made in 2002 in Florida, USA and the seed was sown and grown on in Corindi Beach, NSW, Australia. The new variety was selected in 2004 from among plants located on land at Corindi Beach and has since been named 'C04-014'. Plants of 'C04-014' were propagated by cuttings for further evaluation and resulted to be uniform and stable. The new variety 'C04-014' shows distinctive traits such as late season, strong plant vigor, medium to large fruit of good flavor, firm fruit. The new variety 'C04-014' is intended for use as fresh fruit for shipping, customer pick and processing markets and as a home garden plant.

The new blueberry cultivar is a selection resulting from seedlings produced in a controlled breeding programme of *Vaccinium* varieties in Florida, USA in 2002 from a cross of the blueberry variety known as 'Star' (seed parent) (unpatented) and the blueberry variety known as 'C96-97' (pollen parent) (unpatented). The seed from the cross was sown and grown in Corindi Beach, New South Wales, Australia. The new cultivar was discovered and selected in 2004 as a single plant within a population of seedlings resulted from the controlled cross, in an experimental block in the field at Corindi Beach, New South Wales, Australia, and has since been named 'C04-014.' Selection criteria were a combination of late season, strong plant vigor, medium to large fruit of good flavor and firm fruit. The new variety was subsequently evaluated for a number of years at the commercial farm at Corindi Beach, New South Wales, Australia.

Asexual reproduction of the new variety 'C04-014' by softwood cutting propagation since 2004 at Corindi Beach, New South Wales, Australia has demonstrated that the new variety reproduces true to type with all of the characteristics, as herein described, firmly fixed and retained through successive generations of such asexual propagation, with the clones phenotypically identical to the original plant.

The seed parent 'Star' is characterized by an upright growth habit and early to medium timing of ripening or fruiting. The pollen parent 'C96-97' is characterized by a weak to medium plant growth vigor and firm fruit. The new variety differs from the seed parent 'Star' in that 'C04-014' has later fruiting season. The new variety differs from the pollen parent 'C96-97' in that 'C04-014' has stronger plant vigor. The new variety 'C04-014' has maintained its distinguished characteristics throughout successive asexual propagation.

SUMMARY OF THE INVENTION

The new blueberry variety 'C04-014' originated from the cross of 'Star' (seed parent) (U.S. Plant Pat. No. 10,675) and the variety known as 'C96-97' (pollen parent) (not patented) in 2002 in Florida, USA. The seed parent is characterized by a strongly upright to upright growth habit and medium timing of ripening of fruit. The pollen parent is characterized by a weak-medium plant growth vigor and firm fruit.

The new blueberry variety resulted from seedlings produced in a controlled breeding program. The cross was made in 2002 in Florida, USA and the seed was sown and grown on in Corindi Beach, NSW, Australia.

The new variety was selected in 2004 from among plants located on land at Corindi Beach and has since been named 'C04-014'. Since then plants of 'C04-014' were propagated by cuttings for further evaluation and resulted to be uniform and stable. Asexual reproduction of the new variety by cutting propagation since 2004 at Corindi Beach, NSW, Australia has demonstrated that the new variety reproduces true to type plants.

The new variety was selected in 2004 as a single plant within a population of seedlings resulting from controlled cross of *Vaccinium* varieties. The seedling population was planted in an experimental block in the field at Corindi Beach, NSW, Australia and the selection of the new variety took place in the same block. Selection criteria were a combination of late season, medium plant vigor, medium-large fruit of good flavor and firm fruit. The new variety was subsequently evaluated for a number of years at the commercial farm at Corindi Beach, NSW, Australia.

The following characteristics of the new variety have been repeatedly observed and can be used to distinguish 'C04-014' as a new distinct variety of *Vaccinium corymbosum* hybrid:

1. Late fruiting season
2. Medium plant vigor
3. Upright to semi-upright growth habit
4. Distinct long leaves
5. Medium-large fruit
6. Firm fruit The new variety differs from the female parent 'Star' in that 'C04-014' fruit ripens about a week later and the fruit is of larger size. 'C04-014' differs from the male parent 'C96-97' in that 'C04-014' has stronger plant vigour. The new variety 'C04-014' has maintained its distinguished characteristics throughout successive asexual propagation. The variety has been repeatedly asexually reproduced through softwood cuttings in NSW, Australia and the clones are phenotypically identical to the original plant.

BRIEF DESCRIPTION OF THE DRAWINGS

The accompanying photographic illustration shows typical specimens in full color of the foliage and fruit of the new variety 'C04-014.' The colors are as nearly true as is reasonably possible in a color representation of this type.

Figure 1:
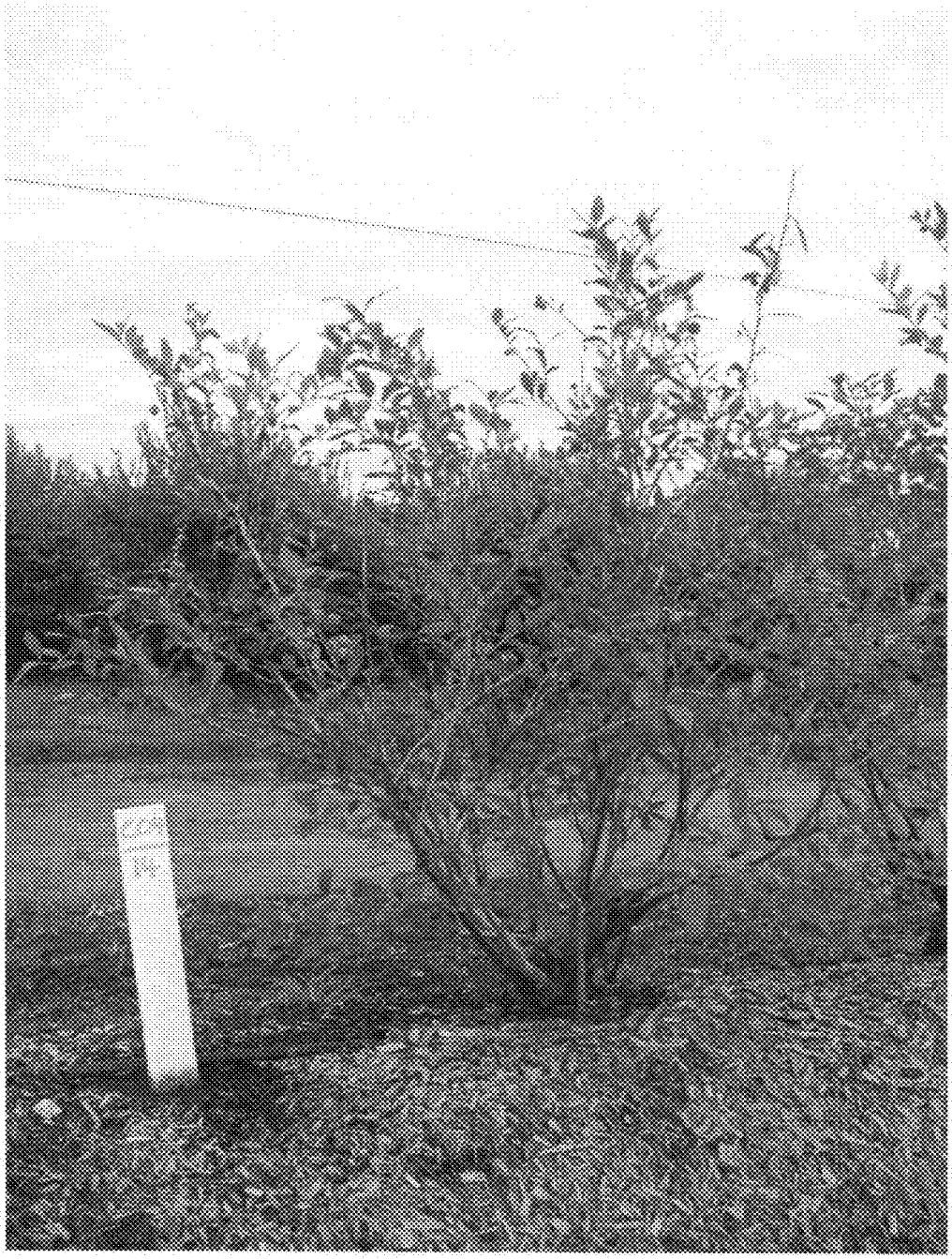
FIG. 1 is a photograph of the new variety 'C04-014,' demonstrating the plant's semi-uptight habit and moderate leafing during the spring.
Figure 2:
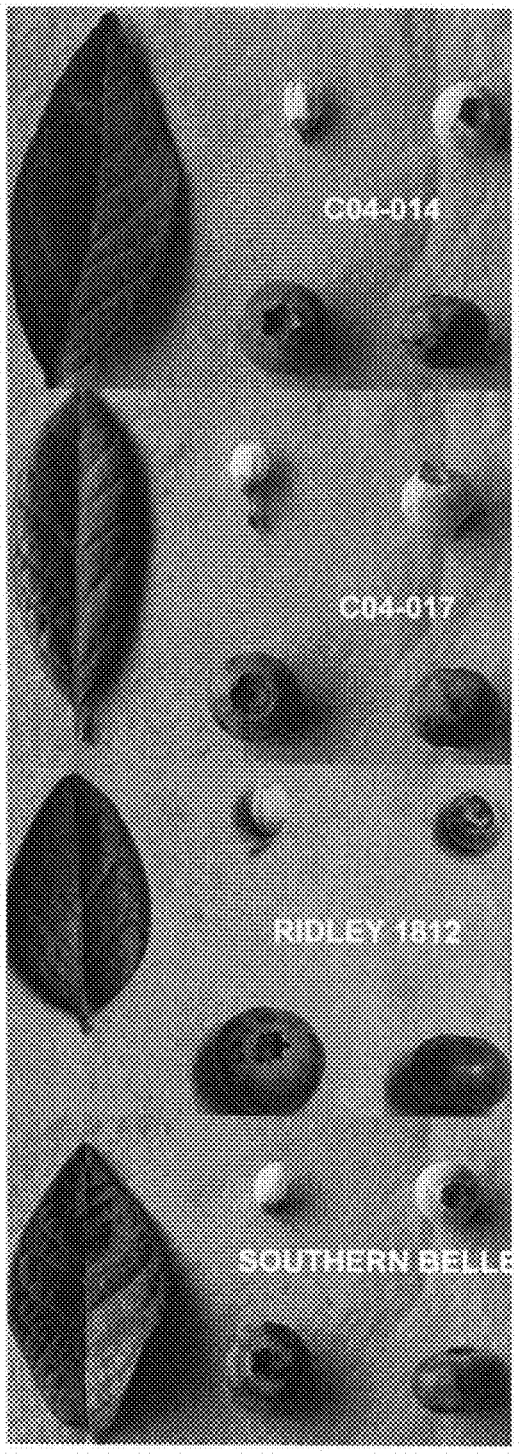
FIG. 2 is a photograph of the new variety 'C04-014,' of the summer foliage of the new variety 'C04-014', showing the typical long leaves showing parts of the plant in comparison with other varieties.
Figure 3:
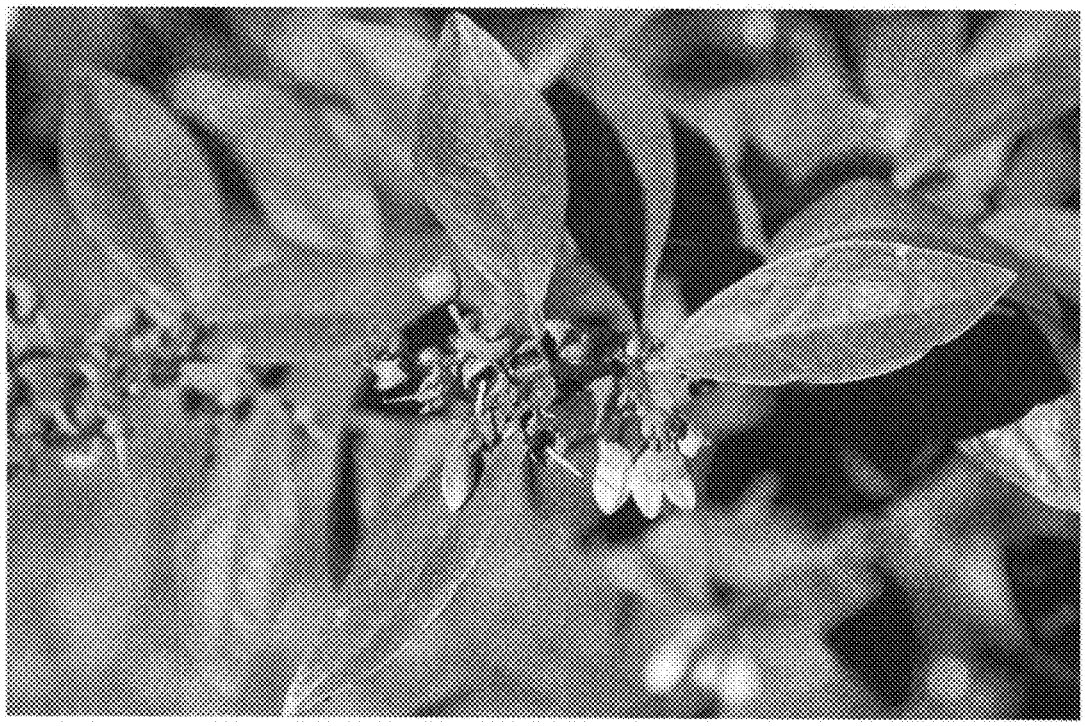
FIG. 3 is a photograph of the flowers of the new variety 'C04-014.'
Figure 4:
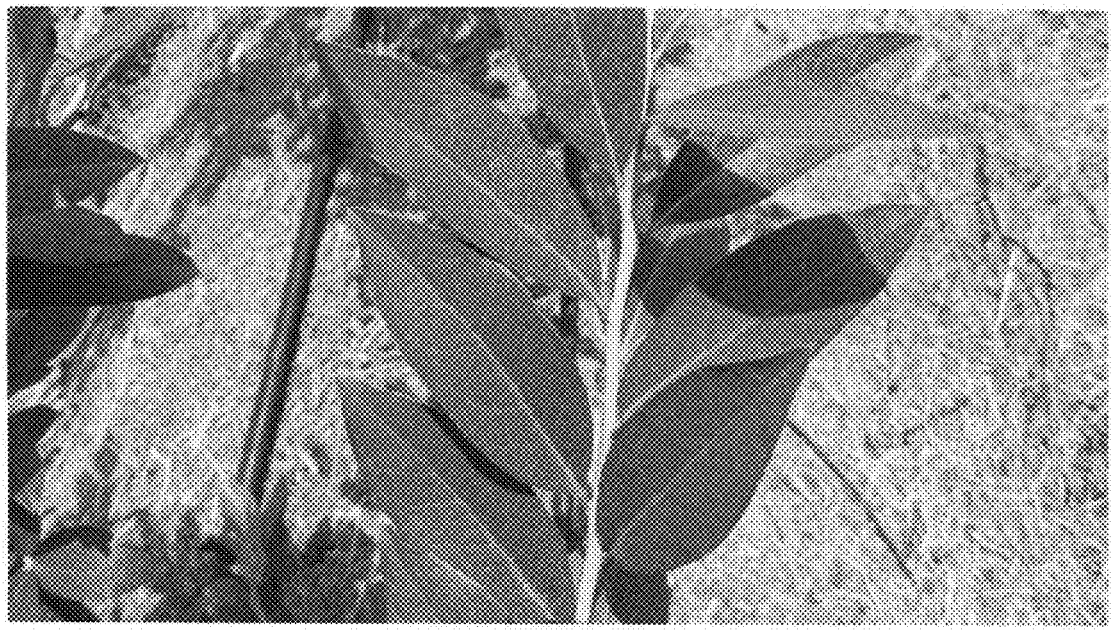
FIG. 4 is a photograph of the fruit, flowers and typical leaf of the new variety 'C04-014.'

The colors in the photographs are as close as possible with the photographic and printing technology utilized. The color values cited in the detailed botanical description accurately describe the colors of the new blueberry.

DETAILED BOTANICAL DESCRIPTION

The following detailed description sets forth the distinctive characteristics of 'C04-014.' The data which defines these characteristics was collected from asexual reproductions of the original selection. Dimensions, sizes, colors, and other characteristics are approximations and averages set forth as accurately as possible. The plant history was taken on plants approximately 4 years of age, and the descriptions relate to plants grown in the field in Corindi Beach, New South Wales, Australia. Descriptions of fruit characteristics were made on fruit grown in Corindi Beach, New South Wales, Australia. Color designations are from R.H.S. Chart—edition 2007.

Classification:

*Family*.—Ericaceae.
*Genus*.—*Vaccinium*.
*Species*.—*corymbosum* hybrid.
*Common name*.—Blueberry.

PLANT

General:

*Parentage*.—'Star'×'C96-97'.
*Plant height*.—Is approximately 1.54 m.
*Plant width*.—Is approximately 0.95 m.
*Growth habit*.—Upright to semi-upright.
*Growth*.—Medium vigour.
*Productivity*.—Medium to high.
*Cold hardiness*.—Low.
*Cold tolerance*.—Low to medium.
*Chilling requirement*.—Low to medium.
*Tolerance to disease*.—It is susceptible to leaf rust.
*Leafing*.—Overall moderate. The plant is deciduous in winter, medium leafing during spring/summer.
*Twigginess*.—Medium to low.

STEM

General:

*Suckering tendency*.—Overall low.
*Mature cane color*.—Near to greyed orange group 166C.
*Mature cane length*.—Is approximately 0.6 m.
*Mature cane width*.—Is approximately 11 mm.
*Bark texture*.—Very smooth.
*Fall color on new shoots*.—The under colour is near to yellow green group 145A; the over colour is near to greyed purple group 184A.
*Surface texture of new wood*.—Very smooth.
*Internode length on strong, new shoots*.—Is approximately 32 mm.
*Fruiting wood*.—Is approximately 35.6 cm in length.

FOLIAGE

General:

*Time of beginning of leaf bud burst*.—Generally late in the season similar to that of 'Star', around the first week of September.
*Leaf color* (*top side*).—Similar to green group 137A and the vein colour similar to yellow-green group 145B.
*Leaf color* (*under side*).—Similar to yellow green group 146C.
*Leaf arrangement*.—Alternate.
*Leaf shape*.—Elliptic.
*Leaf margins*.—Minor serration.

*Undulation of margin*.—Very weak to weak.
*Leaf venation*.—Reticulate.
*Leaf apices*.—Acute.
*Leaf bases*.—Cuneate.
*Leaf length*.—Long, average 88.2 mm (range 76-95 mm).
*Leaf width*.—Average 37 mm (range 28-44 mm).
*Leaf length/width ratio*.—2.3.
*Leaf nectarines*.—Absent.
*Pubescence of upper side*.—Absent.
*Pubescence of lower side*.—Absent.
*Cross sectional profile*.—Flat.
*Longitudinal profile*.—Straight.
*Attitude*.—Horizontal.

Petioles:
*Length*.—Average 5.41 mm.
*Width*.—1.57 mm.
*Color*.—Similar to greyed purple group 187B.

FLOWERS

General:
*Time of beginning of flowering*.—Late.
*Time of* 50% *anthesis*.—Average 15$^{th}$ August.
*Flower shape*.—Urceolate.
*Flower bud density*.—Sparse.
*Flower fragrance*.—Absent.
*Flower arrangement*.—Alternately.
*Flower type*.—Complete flower, having sepals, petals, stamens and pistils.

Corolla:
*Color*.—White group 155A.
*Length*.—Average 8.5 mm.
*Width*.—Average 7.2 mm.
*Aperture width*.—Average 4.4 mm.
*Anthocyanin coloration of corolla*.—Absent.
*Corolla ridges*.—Present.
*Protrusion of stigma*.—Absent.
*Corolla shape*.—Urceolate Inflorescence:
*Length*.—30-40 mm.
*Diameter*.—13-20 mm.
*Length of peduncle*.—12.3 mm.
*Surface texture of peduncle*.—Smooth.
*Color of peduncle*.—Yellow green group 146D.
*Length of pedicel*.—8.9 mm.
*Surface texture of pedicel*.—Smooth.
*Color of pedicel*.—Yellow green group 146D.
*Number of flowers per cluster*.—5.
*Flower cluster density*.—Medium to sparse.

Calyx (with sepals):
*Diameter*.—6.9 mm.

Stamen:
*Length*.—7.2 mm.
*Number per flower*.—10.
*Filament color*.—Yellow-green group N144D.

Style:
*Length*.—9.13 mm.
*Color*.—Yellow-green group 144D.

Pistil:
*Length*.—11.6 mm.
*Ovary color* (*exterior*).—Green group 143C.

Anther:
*Length*.—4.29 mm.
*Number*.—10.
*Color*.—Greyed-orange group 167A.

Pollen:
*Abundance*.—Medium.
*Color*.—Yellow group 4D.
*Self-compatibility*.—Overall good, producing somewhat smaller fruit (2 g).

FRUIT

General:
*Time of fruit ripening*.—Late season.
*Time of* 50% *maturity*.—Average 1$^{th}$ November.
*Fruit development period*.—Average 69 days.
*Cluster density*.—Medium to sparse with 3-6 berries per cluster.
*Unripe fruit color*.—Similar to yellow-green group 143B.
*Ripe berry color*.—Similar to Blue group 102A.
*Berry surface wax abundance*.—Medium to strong.
*Berry flesh color*.—Yellow-green group 145B.
*Berry weight*.—Average 2.6 (ranging between 2.3 to 3 g).
*Berry height from calyx to scar*.—Average 13.5 mm.
*Berry diameter*.—Average 17.2 mm.
*Berry shape*.—Oblate.
*Fruit stem scar*.—Medium to small and dry.
*Sweetness when ripe*.—Low to medium.
*Firmness when ripe*.—High.
*Acidity when ripe*.—Medium.
*Storage quality*.—Medium.
*Suitability for mechanical harvesting*.—Not tested.
*Self-fruitfulness*.—High.
*Uses*.—Fresh fruit.

SEED

General:
*Seed abundance in fruit*.—Low, similar to 'Star'.
*Seed number*.—Average of 75 in 10 fruit.
*Seed color*.—Greyed-orange group 166A.
*Seed length*.—Average 1.95 mm (range 1.6-2.2 mm).

COMPARISON BETWEEN PARENTAL AND COMMERCIAL CULTIVARS

| | Variety | Comparator variety | | | | |
|---|---|---|---|---|---|---|
| Characteristic | C04-014 | C99-042 | Emerald | C97-390 | Star | Snow-chaser |
| Soluble solid content (%) | 12.5 | 13.1 | 11.6 | 12.2 | 13.1 | 14.3 |
| Titratable acidity (%) | 0.4 | 0.3 | 0.5 | 0.3 | 0.4 | 0.5 |
| Fruit weight (g) | 2.6 | 1.9 | 3.0 | 2.0 | 1.9 | 1.7 |
| Firmness (g/mm) | 212 | 273 | 187 | 211 | 210 | 188 |
| Shelf life (days) | 30 | 23 | 20 | 24 | 35 | 25 |
| Plant habit | Upright to semi-upright | Semi-upright to spreading | Spread-ing | Semi-upright | Strongly upright to upright | Semi-upright |
| Time of fruit ripening | Late | Early | Mid to late | Early | Late | Very early |

The invention claimed is:

1. A new and distinct variety of blueberry plant named 'C04-014,' substantially as illustrated and described herein.

* * * * *